(12) United States Patent
Henninger et al.

(10) Patent No.: US 8,585,760 B2
(45) Date of Patent: Nov. 19, 2013

(54) VERTEBRAL COLUMN IMPLANT CONSISTING OF BONE MATERIAL

(75) Inventors: Jürgen Henninger, Offenbach (DE); Klaus Landis, Heroldsberg (DE)

(73) Assignee: Tutogen Medical GmbH, Neunkirchen am Brand (DE)

( * ) Notice: Subject to any disclaimer, the term of this patent is extended or adjusted under 35 U.S.C. 154(b) by 1579 days.

(21) Appl. No.: 10/513,531

(22) PCT Filed: Apr. 2, 2003

(86) PCT No.: PCT/EP03/03452
§ 371 (c)(1),
(2), (4) Date: Nov. 5, 2004

(87) PCT Pub. No.: WO03/092559
PCT Pub. Date: Nov. 13, 2003

(65) Prior Publication Data
US 2006/0036321 A1    Feb. 16, 2006

(30) Foreign Application Priority Data
May 6, 2002   (DE) .................................. 102 20 139

(51) Int. Cl.
*A61F 2/44*   (2006.01)

(52) U.S. Cl.
USPC ..................................................... 623/17.11

(58) Field of Classification Search
USPC ............................................. 623/17.11–17.16
See application file for complete search history.

(56) References Cited

U.S. PATENT DOCUMENTS

| 4,300,243 | A | 11/1981 | Baumgartner | 3/1 |
| 5,989,289 | A | 11/1999 | Coates et al. | 623/17 |
| 6,174,311 | B1* | 1/2001 | Branch et al. | 606/61 |
| 6,206,923 | B1 | 3/2001 | Boyd et al. | 623/17.11 |
| 6,261,586 | B1* | 7/2001 | McKay | 424/423 |
| 6,277,149 | B1* | 8/2001 | Boyle et al. | 623/17.16 |
| 6,419,945 | B1* | 7/2002 | Gresser et al. | 424/426 |
| 2002/0026242 | A1 | 2/2002 | Boyle et al. | 623/17.11 |

FOREIGN PATENT DOCUMENTS

| DE | 299 13 200 U1 | 10/1999 |
| DE | 198 26 619 A1 | 12/1999 |
| DE | 199 52 939 A1 | 5/2001 |
| WO | WO 99/09914 | 3/1999 |
| WO | WO 00/19941 | 4/2000 |

* cited by examiner

*Primary Examiner* — David Bates
(74) *Attorney, Agent, or Firm* — Gifford, Krass, Sprinkle, Anderson & Citkowski, P.C.

(57) ABSTRACT

The invention relates to a vertebral column implant for intercorporal fusion to the vertebral column. Said implant consists of a body produced from preserved bone material, whose size is adapted to the vertebral interstice between adjacent vertebrae that is formed once the vertebral interbody has been removed. The vertebral column implant exhibits an improved distribution of forces.

4 Claims, 2 Drawing Sheets

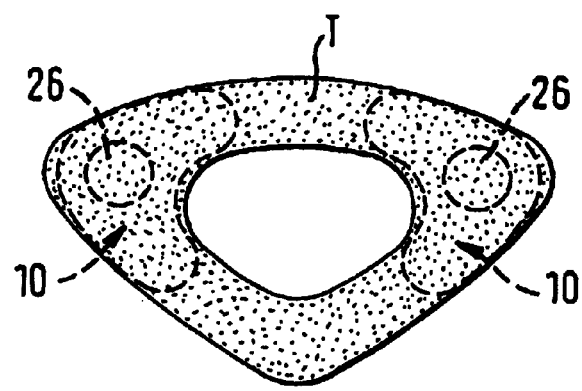
Fig. 5
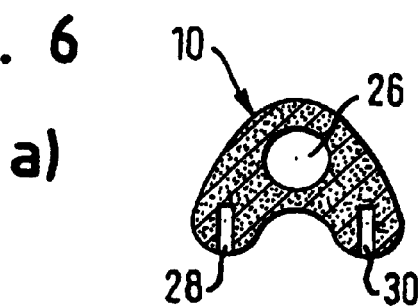
Fig. 6 a)
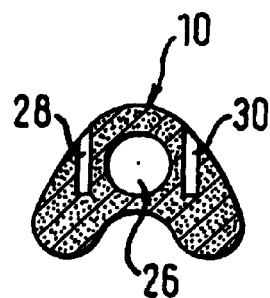
b)
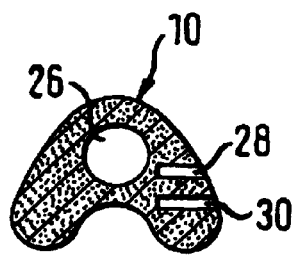
c)

VERTEBRAL COLUMN IMPLANT CONSISTING OF BONE MATERIAL

RELATED APPLICATIONS

This application is the U.S. National Phase of PCT/EP03/03452 filed Apr. 2, 2003, which in turn claims priority of German Patent Application DE 102 20 139.0 filed May 6, 2002, the contents of which are incorporated herein by reference.

FIELD OF THE INVENTION

The present invention relates to an implant for the connection of bones and in particular to a spinal column implant for the interbody fusion of vertebrae which is inserted between two vertebrae to be fused.

BACKGROUND OF THE INVENTION

An existing implant for the fusion of bones requires an improved distribution of force between two vertebrae to be fused.

SUMMARY OF THE INVENTION

A spinal column implant is detailed for interbody fusion to the spinal column. The implant includes a body of preserved bone material having a substantially rectangular or trapezoidal cross section. The implant is adapted to fill the intervertebral space between adjoining vertebrae created after removal of the intervertebral body. The body of the implant has two limbs extending therefrom at an acute angle and a transverse web connecting the two limbs.

BRIEF DESCRIPTION OF THE DRAWINGS

FIG. 5 is a cross-section through a tibia bone with inscribed contours of the spinal column implant in accordance with the invention; and FIG. 6 is a plan view of embodiments of a spinal column implant in accordance with the present invention with possible bores for the reception of an application tool.

DETAILED DESCRIPTION OF THE PREFERRED EMBODIMENTS

Figure 1:
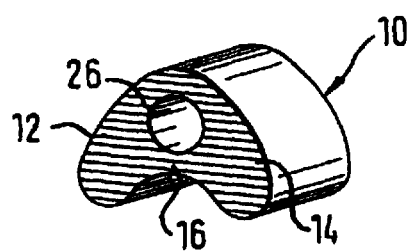
FIG. 1 is a perspective view of an embodiment of a spinal column implant in accordance with the invention.

A particular advantage of the spinal column implant in accordance with the invention is provided by the material used which, on the basis of its biological origin and its preservation, does not represent a foreign body antigen. The advantage furthermore results by an A-shaped design with two limbs that the implant is adapted to the shape of the edges of vertebral bodies, in particular of cervical vertebrae, and thus automatically comes into the correct position on insertion into the intervertebral space. The implant is particularly well matched to the natural shape of the end plates of the vertebral bodies by the specific shape in accordance with the invention and thus provides the largest possible contact surface to the end plates due to the A shape. A more physiological distribution of the forces thereby takes place, whereby pressure peaks and a sinking of the implant into the vertebral bodies caused by this are avoided.

The A shape is also particularly advantageous since bone powder loosely introduced both between the ends of the limbs and in the central opening is transported with the implant into the intervertebral space. In this manner, when the implant is inserted into the intervertebral space, bone powder or spongeous bone or the like can be introduced into the region of the implant.

In a first advantageous embodiment of the spinal column implant in accordance with the invention, the body has only rounded outer edges. Such a design of the body facilitates the application of the spinal column implant between the vertebral bodies to be fused in that the roundings prevent a canting of the implant during the application.

In accordance with a further advantageous embodiment of the invention, a limb of the body has a convexly curved outer contour. A particularly good adaptation to end plates of the vertebral bodies takes place by such a design of the outer surfaces. The ends of the limbs can also be rounded, in particular rounded in approximately semi-circular shape, which promotes the insertion of the implant and its easy and correct positioning.

In accordance with a further embodiment of the invention, the opening formed by the limbs and by the transverse web has a rounded peripheral contour, in particular an approximately circular peripheral contour. A central opening shaped in this manner can be manufactured particularly easily, on the one hand; the implant is hereby provided with a particularly high stability, on the other hand.

In accordance with a further embodiment of the invention, the central opening formed by the limbs and by the transverse web does not extend in a through manner from the front side to the rear side of the body. This opening can, for example, be provided with a base or with an intermediate base, whereby the stability of the body is increased, on the one hand, and a receiving space for bone powder can be formed, on the other hand.

In accordance with a further embodiment of the invention, the outer contour of the body can have a central concave section in the region of the transverse web and of the free ends of the limbs adjoining it. This section can serve the purpose of introducing bone powder or bone chips into the intervertebral space with the introduction of the implant.

In accordance with a further embodiment of the invention, the outer surfaces of the two limbs include an angle of approximately 40 to 70° with one another. A particularly good adaptation to the intervertebral space between adjacent cervical vertebrae thereby takes place. A correct positioning is thus automatically provided by such a curvature of the implant. Provided that the spinal column implant has a trapezoidal cross-section, as in accordance with a further advantageous embodiment, the reestablishing of the physiological curvature of the spinal column is hereby also possible.

The spinal column implant in accordance with the invention is preferably made substantially symmetrical. However, an asymmetric shape is also possible in which the design of the two limbs differs from one another.

In accordance with a further advantageous embodiment, the body can be formed of compact bone material, with spongeous bone material being located in the opening formed by the limbs and by the transverse web. The fusion of the adjacent vertebrae can be facilitated by such an "inner core" of spongiosa.

In accordance with a further embodiment of the present invention, receiving bores can be provided at one or more sides of the body. Application tools can then be introduced into these bores in order to introduce the implant between the vertebrae to be fused in a precisely positioned manner.

The body can, in accordance with the invention, be formed of processed, preserved and sterile bone material of human origin, a so-called allograft, or of processed, preserved and sterile bone material of animal origin, a so-called xenograft. The body can be made from solid cortical bone material or also from solid spongeous bone material, for example from the humerus, the femur, the tibia or another bone either from dead people or from animals, in particular from bone material from cattle.

A suitable allogenic or xenogenic bone material is processed as the material for the spinal column implant in accordance with the present invention such that it is preserved, suitable for storage and sterile and can be used in accordance with its purpose. The preservation of the bone material can take place, for example, by freeze drying. Another preferred method of manufacturing the bone material is processing by preferably solvent dehydration of native bone material by means of an organic solvent miscible with water, e.g. methanol, ethanol, propanol, isopropanol, acetone, methyl ethyl ketone or mixtures of these solvents. The preservation and sterilization of the bone material in accordance with this method is also the subject of patent DE 29 06 650, whose content is incorporated by reference herein.

This method serves for the manufacture of preserved transplants and permits a dehydration and exposure down to the fine structure of the fibril of the bone material so that the processed bone material in the histological image has a morphological structure very similar to the natural bone and so that thus the desired properties of the bone material are maintained. This method of solvent dehydration moreover has the advantage that a much lower apparatus effort is required in comparison with freeze drying.

The bone material can furthermore also be produced by solvent dehydration of native bone with a subsequent terminal sterilization, in particular by irradiation with gamma rays. Alternatively, the spongeous material can be produced by aseptic processing of bone material without terminal sterilization. The starting material of the bone implant in accordance with the invention is human or animal bone of sufficient size.

The bone is subjected to an osmotic treatment to remove the antigenity. An oxidizing treatment is furthermore carried out for the denaturing of solvent proteins. To optimize the virus inactivation, a pH lowering to pH 3 can take place or a treatment with caustic soda or with another substance which destroys DNA/RNA. The dehydration takes place by organic solvents, preferably acetone. The subsequent sterilization takes place by high-energy radiation, preferably γ rays with a maximum dose of 25 kGy.

A bone treated in this manner maintains its natural mineral/collagen compound and its properties. A bone treated in this manner is moreover capable of reconversion.

The spinal column implant in accordance with the invention can in particular advantageously be manufactured by a method in which human or animal tibia bone is sawn into at least one slice transverse to the longitudinal axis of the bone from which the two spinal column implant bodies are formed. This method is based on the recognition that the outer contour of the tibia bone is very similar to that of the spinal column implant body in accordance with the invention so that the shape of the implant body in accordance with the invention can be advantageously inscribed into the tibia bone.

In the Figures, the same reference numerals designate the same components of the embodiments shown in each case.

The embodiment shown in FIG. 1 of a spinal column implant in accordance with the invention includes a body 10 which includes, for example, of cortical, diaphyseal bone material, e.g. of human origin.

The body 10 shown in FIG. 1 has two limbs 12 and 14 extending at an acute angle α (FIG. 3), with a transverse web 16 connecting the limbs being provided between the limbs 12 and 14 so that the body 10 essentially has the shape of an A in plan view.

Figure 3:
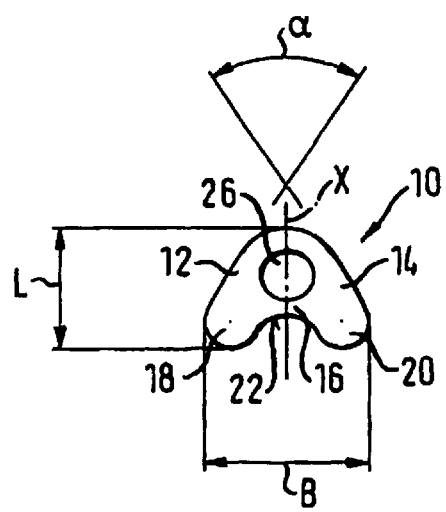
FIG. 3 is a plan view of a further embodiment of a spinal column implant in accordance with the invention.

As FIG. 1, and in particular FIG. 3, shows, the outer contour of the "A" has only rounded edges. The limbs 12 and 14 moreover have a slightly convexly curved outer contour. As can furthermore be recognized, the width of the limbs 12 and 14 is not uniform over the longitudinal extent. The two limbs 12 and 14 are rather relatively wide at their outer free ends. A lower width of the limbs is present, in contrast, in the region of the apex of the A.

The free ends 18, 20 of the limbs 12 and 14 (FIG. 3) are rounded in approximately semi-circular shape. The outer contour of the body 10 in the region of the transverse web 16 and of the adjoining free ends 18, 20 of the limbs 12, 14 has a concave section 22 which constantly merges into the otherwise completely convexly curved peripheral contour of the body 10.

Figure 2:
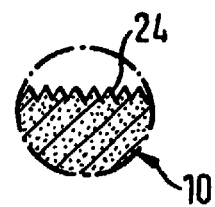
FIG. 2 is an enlarged representation of the surface texture of the implant from FIG. 1.

As FIGS. 1 and 2 show, the shown upper side or also the lower side of the body 10 can have a grooving 14 which prevents a dislocation of the implant in the intervertebral space.

The embodiments of the spinal column implant in accordance with the invention shown in the Figures are made symmetrically to its central axis X. It must, however, also be pointed out that asymmetrical embodiments are also feasible here in which, for example, the length or the design of the two limbs 18 and 20 is different.

As the Figures furthermore show, an opening 26 is formed by the two limbs 12 and 14 and by the transverse web 16 which has a through hole from the front side to the rear side of the body 10 in the embodiment shown and is made with a circular cross-section.

FIG. 3 shows a plan view of an embodiment of a body 10 of a spinal column implant, with the width B, the length L and the height H (FIG. 4b)) being able to be selected as follows: for lumbar applications, the length L can amount to approximately 30 to 60 mm, the width B to approximately 8 to 20 mm and the height H to approximately 6 to 18 mm. For cervical applications, the length L can amount to approximately 8 to 18 mm, the width B to approximately 8 to 18 mm and the height H to approximately 4 to 15 mm. In the embodiment shown in FIG. 3, the length L amounts to approximately 11 mm, the width B to approximately 14 mm and the height H to approximately 8 mm.

The angle α which the outer surfaces of the two limbs 12 and 14 include with one another preferably lies in a range from approximately 40 to 70°. In the embodiment shown in FIG. 3, the angle α amounts to approximately 55°.

Figure 4:
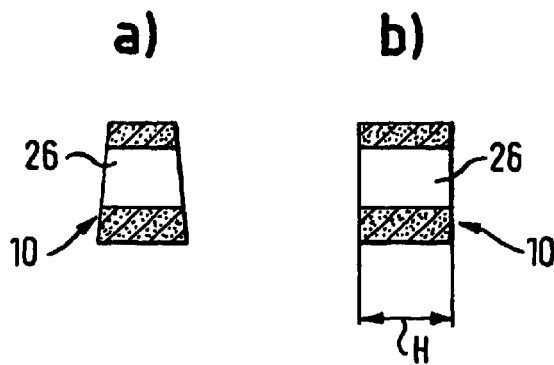
FIG. 4 is possible cross-sectional shapes of the spinal column implant in accordance with the invention.

FIGS. 4a) and 4b) show possible cross-sectional shapes of the body 10 along the central axis X of FIG. 3. As can be recognized from FIG. 4a), the cross-section of the body 10 can be trapezoidal or, as is shown in FIG. 4b), substantially rectangular. The obliquely extending sides shown in FIG. 4a) can deviate from the rectangular form at an angle from approximately 3 to 6°. It must again be pointed out at this point that the representation of FIG. 4 is not in scale to that of FIG. 3.

There is generally the possibility that the spinal column implant in accordance with the invention is made as a solid piece, for example from cortical or from spongeous bone. An alternative embodiment of the invention provides that the spinal column implant—likewise made from cortical or spongeous bone—is made as a hollow body.

FIG. 5 shows a tibia bone T in cross-section, with the outer contours of two spinal column implants 10 being inscribed into the tibial cross-section in accordance with the invention. An opening is bored into each of the implants 10. As can easily be recognized, the tibia bone is suited in a particularly easy manner for the manufacture of the spinal column implant body in accordance with the invention, since the outer contour and the inner contour of the tibia bone T almost corresponds to the outer contour of the body 10. In a particularly advantageous method for the manufacture of the body 10, human or animal tibia bone is therefore sawn into slices transverse to the bone longitudinal axis, with two bodies 10 shown in the Figures being formed from the slice of bone obtained in this manner, for example by milling. A method for the manufacture of a material for implants is described in WO 00/19941 A.

FIGS. 6a) to c) show different embodiments of a spinal column implant 10 with hole bores 28, 30 for the reception in an application tool. The hole bores can have different depths and stand at different angles to one another. It is also possible to provide only one hole bore. Generally, the hole bores are provided in that plane in which the spinal column implant can be introduced into the intervertebral space. Depending on the type of application, the hole bores 28, 30 are positioned at the free ends of the limbs 12, 14 (FIG. 6a)), in the region of the acute end of the "A" (FIG. 6b)) or at a side of the limbs 12, 14 (FIG. 6c)).

The invention claimed is:

1. A method for the manufacture of a spinal column implant, comprising sawing a human or animal tibia bone transversely to the bone longitudinal axis into at least one slice; forming two bodies (10) from the at least one slice; boring an opening into one of the two bodies; and packing the opening with spongeous bone material, wherein the two bodies (10) each comprises an upper side, a lower side, and at least one outer surface, wherein the two bodies (10) are adapted to the intervertebral space between adjoining vertebrae after removal of the intervertebral body, wherein the upper and lower sides face the adjoining vertebrae and define two limbs (12, 14) each having ends (18, 20) extending at an acute angle ($\alpha$) in the approximate range of 40-70° and a transverse web (16) connecting the limbs (12, 14) so that each of the two bodies (10) substantially has the shape of an A in plan view.

2. A method for the manufacture of a spinal column implant in accordance with claim 1 characterized in the bone being a bovine bone and the implant maintains mineral and collagen compound of the bone.

3. A method for the manufacture of a spinal column implant in accordance with claim 1 further comprising boring an opening into one of the two bodies.

4. A method for the manufacture of a spinal column implant in accordance with claim 1 further comprising rounding edges on one of the two bodies.

* * * * *